(12) United States Patent
Harrison et al.

(10) Patent No.: US 6,207,420 B1
(45) Date of Patent: *Mar. 27, 2001

(54) **FUSION PROTEIN SYSTEMS DESIGNED TO INCREASE SOLUBLE CYTOPLASMIC EXPRESSION OF HETEROLOGOUS PROTEINS IN *ESCHERICHIA COLI***

(75) Inventors: Roger G. Harrison, Norman, OK (US); Gregory D. Davis, Mountain View, CA (US)

(73) Assignee: The Board of Regents of the University of Oklahoma

(*) Notice: Subject to any disclaimer, the term of this patent is extended or adjusted under 35 U.S.C. 154(b) by 0 days.

This patent is subject to a terminal disclaimer.

(21) Appl. No.: 09/448,224

(22) Filed: Nov. 23, 1999

Related U.S. Application Data

(63) Continuation of application No. 09/149,725, filed on Sep. 8, 1998, now Pat. No. 5,989,868.
(60) Provisional application No. 60/058,698, filed on Sep. 12, 1997, and provisional application No. 60/088,699, filed on Jun. 9, 1998.

(51) Int. Cl.$^7$ .............................. C12P 21/02; C12N 1/21; C12N 15/64; C12N 15/62; C07H 21/04

(52) U.S. Cl. ..................... 435/69.7; 536/23.1; 536/23.4; 536/24.1; 530/350; 435/69.1; 435/252.3; 435/254.11; 435/252.33; 435/91.4; 435/320.1; 435/325; 435/348

(58) Field of Search .................................. 435/69.7, 69.1, 435/252.3, 254.11, 320.1, 325, 348, 252.33, 91.4; 536/23.1, 23.4, 24.1; 530/350

(56) References Cited

U.S. PATENT DOCUMENTS

| | | | |
|---|---|---|---|
| 5,270,181 | 12/1993 | McCoy et al. | 435/69.7 |
| 5,292,646 | 3/1994 | McCoy et al. | 435/69.7 |

FOREIGN PATENT DOCUMENTS

| | | |
|---|---|---|
| 9402502 | 2/1994 | (WO). |

OTHER PUBLICATIONS

"Phage Display/Protein Fusion", *New England BioLabs*, 1996/1997 Catalog, pp. 163–165.
"Expression Systems", *Invitrogen Product Catalog*, 1997, 6 pages.
"Recombinant Protein Expression", *Pharmacia Biotech Catalog*, 1997, pp. 159–163.
David L. Wilkinson and Roger G. Harrison, "Predicting the Solubility of Recombinant Proteins in *Escherichia Coli*", *Biotechnology*, 9:443–448, May 1991.
Donahue et al., "Human IL–3 and GM–CSF Act Synergistically in Stimulating Hematopoiesis in Primates", *Science*, 241:1820–1823, Sep. 1988.
Lutsenko et al., "Recombinant Interleukin–3 Expression System in *E. coli*", http://www.ncbi.nlm.nih.gov/htbin–post/Entrez/query?uid=1524590&form=6&db=m&Dopt=r, *Bioorg Khim*, 18 (3) :391–397, Mar. 18, 1992 (page one only).
George et al., "High–Level Expression in *Escherichia coli* in Biologically Active Bovine Growth Hormone", *DNA*, 4(4) :273–281, 1985.
Joost Haelewyn and Marc De Ley, "A Rapid Single–Step Purification Method for Human Interferon–γ from Isolated *Escherichia coli* Inclusion Bodies", *Biochemistry and Molecular Biology International*, 37 (6) :1163–1171, Dec. 1995.
Sharma et al., "Folding and Activation of Recombinant Human Prorenin", *Biotechnology and Applied Biochemistry*, 9:181–193, 1987.
Guan et al., "Vectors That Facilitate the Expression and Purification of Foreign Peptides in *Escherichia coli* by Fusion to Maltose–Binding Protein", *Gene*, 67:21–30, 1988.
Zhang et al., "Expression and Functionqal Characterization of *Escherichia coli* NusQ and Lambda Q as Glutathione S–Transferase Fusion Proteins", *Protein Expr Purif*, 6 (5) :625–631, Oct. 1995.
George Georgiou and Pascal Valax, "Expression of Correctly Folded Proteins in *Escherichia coli*", *Current Opinion in Biotechnology*, 7:190–197, 1996.
LaVallie et al., "A Thioredoxin Gene Fusion Expression System That Circumvents Inclusion Body Formation in the *E. coli* Cytoplasm", *Bio/Technology*, 11:187–193, Feb. 11, 1993.

*Primary Examiner*—Robert A. Schwartzman
*Assistant Examiner*—Lisa Gansheroff
(74) *Attorney, Agent, or Firm*—Dunlap, Codding and Rogers, P.C.

(57) ABSTRACT

A fusion sequence having a carrier protein which is preferably an *E. coli* protein having a predicted solubility probability of at least 90% fused to a target heterologous peptide or protein, and a host cell (especially *E. coli*) transformed with, or having integrated into its genome, a DNA sequence comprising a DNA encoding a carrier protein as defined herein fused to the DNA sequence of a selected heterologous peptide or protein. This fusion sequence is under the control of an expression control sequence capable of directing the expression of a fusion protein in the cell. An objective of the present invention is to improve the purification process of recombinant fusion proteins by avoiding the initial expression of these fusion proteins in *E. coli* as insoluble inclusion bodies. The methods and compositions of the present invention permit the production of large amounts of heterologous peptides or proteins in a stable, soluble form in certain host cells which normally express limited amounts of such soluble peptides or proteins. The present invention produces fusion proteins which retain the desirable characteristics of a carrier protein (i.e., stability, solubility, and a high level of expression).

24 Claims, 6 Drawing Sheets

OTHER PUBLICATIONS

Donald Smith and Kevin Johnson, "Single–Step Purification of Polypeptides Expressed in *Escherichia coli* As Fusion With Glutathione S–Transferase", *Gene*, 67:31–40, 1988.

Blattner et al., "The Complete Genome Sequence of *Escherichia coli* K–12", *Science*, vol. 277, pp. 1453–1462, XP002069950, Sep. 5, 1997.

Davis, G.D. et al., "Soluble Expression of Recombinant Proteins in *Escherichia Coli* Using the NUSA Expression System", *Abstracts of Papers of the American Chemical Society*, vol. 216, No. 1–3, pp. 103–btec, XP002089994, Aug. 23, 1998.

Davis, G.D. and Harrison, R.G., "Rapid Screening of Fusion Protein Recombinants by Measuring Effects of Protein Overexpression on Cell Growth", *Biotechniques*, vol. 24, No. 3, pp. 360–362, XP002089507, Mar. 1998.

Wilkinson, D.L. and Harrison, R.G., "Predicting the Solubility of Recombinant Proteins in *Escherichia Coli*", *Biotechnology*, vol. 9, pp. 443–448, XP002089506, May 1991.

FUSION PROTEIN SYSTEMS DESIGNED TO INCREASE SOLUBLE CYTOPLASMIC EXPRESSION OF HETEROLOGOUS PROTEINS IN ESCHERICHIA COLI

CROSS-REFERENCE TO RELATED APPLICATIONS

This application is a continuation of U.S. Ser. No. 09/149,725, filed Sep. 8, 1998, now U.S. Pat. No. 5,989,868, which claims the benefit of U.S. Provisional Application Ser. No. 60/058,698, filed Sep. 12, 1997, and also claims the benefit of U.S. Provisional Application Ser. No. 60/088,699, filed Jun. 9, 1998.

BACKGROUND

The present invention relates to recombinant methods of producing fusion proteins using E. coli proteins as carrier proteins for producing soluble fusion proteins.

A major benefit resulting from the advent of recombinant DNA technology has been the large scale production of proteins of medical or industrial importance. The simplest and most inexpensive means available for obtaining large amounts of proteins by recombinant DNA technology is by expression of protein genes in bacteria (Georgiou and Valax, 1996). The efficient synthesis of heterologous proteins in the bacterium Escherichia coli has now become routine. However, when high expression levels are achieved, recombinant proteins are frequently expressed in E. coli as insoluble protein aggregates termed "inclusion bodies." Although initial purification of inclusion body material is relatively simple, the protein must be subsequently refolded into an active form, which is typically a cumbersome trial-and-error process (Georgiou and Valax, 1996). Thus, it is much more desirable to express the recombinant protein in soluble form.

A strategy to avoid inclusion body formation is to fuse the protein of interest (i.e. the target protein) to a protein known to be expressed at substantial levels in soluble form in E. coli (i.e. the carrier protein). The most widely used carrier protein for the purpose of solubilization is thioredoxin from E. coli (LaVallie et al., 1993). A fusion protein system using thioredoxin for solubilization of target proteins is now being marketed by Invitrogen Corporation (Carlsbad, Calif.). However, despite being touted for its ability to solubilize proteins in a fusion protein, thioredoxin does not always lead to formation of a fusion protein which is soluble at the normal E. coli growth temperature of 37° C. LaVallie et al. (1993) used thioredoxin as a carrier protein to express 11 human and murine cytokines. Of the 11 proteins, only 4 were expressed in soluble form as thioredoxin fusions at 37° C. The non-soluble fusion proteins with thioredoxin could be expressed in soluble form by reducing the growth temperature for expression to as low as 15° C. Several problems with the use of thioredoxin fusions for protein solubilization for any protein are apparent. For example, having to reduce the expression temperature to as low as 15° C. may give unacceptable low rates of protein expression and slow growth rates. Also, due to the small size of thioredoxin (11.7 kilodaltons), fusions with larger proteins may not be soluble; that is, thioredoxin may not be large enough to compensate for the insolubility of a large protein.

Two other E. coli fusion protein systems are widely used: fusions with E. coli maltose-binding protein (Guan et al., 1988), which is 40 kilodaltons in size, and fusions with Schistosoma japonicum glutathione S-transferase (Smith and Johnson, 198.8), 26 kilodaltons in size. Both of these systems were developed with the objective of enabling an affinity purification of the fusion protein to be carried out. Both systems tend to give soluble fusion proteins but fail to do so approximately 25% of the time (New England Biolabs Tech Data Sheet, 1992; Smith and Johnson, 1988). Thus, thioredoxin fusions appear to be more soluble than either maltose-binding protein fusions or glutathione S-transferase fusions. An E. coli fusion protein system which could be reliably produced in a soluble form would be desirable.

SUMMARY OF THE INVENTION

In one aspect, the present invention provides a fusion sequence comprising a carrier protein comprising an E. coli protein having a predicted solubility probability of at least 90% fused to a target heterologous peptide or protein. The peptide or protein may be fused to the amino terminus of the soluble protein or the carboxyl terminus of the soluble protein. The fusion sequence according to this invention may optionally contain a linker peptide between the carrier protein and the selected peptide or protein. This linker provides, where needed, a selected cleavage site or a stretch of amino acids capable of preventing steric hindrance between the carrier protein and the target peptide or protein.

In another aspect, the present invention provides a DNA molecule encoding the fusion sequence defined above in association with, and under the control of, an expression control sequence capable of directing the expression of the fusion protein in a desired host cell, in particular, E. coli.

Still a further aspect of the invention is a host cell (especially E. coli) transformed with, or having integrated into its genome, a DNA sequence comprising a DNA encoding a carrier protein as defined herein fused to the DNA sequence of a selected heterologous peptide or protein. This fusion sequence is desirably under the control of an expression control sequence capable of directing the expression of a fusion protein in the cell.

In yet another aspect, there is provided herein a novel method for increasing the expression of soluble recombinant proteins. The method includes culturing under suitable conditions the above-described host cell to produce the fusion protein.

In one embodiment of the method contemplated herein, if the resulting fusion protein is cytoplasmic, the cell can be lysed by conventional means to obtain the soluble fusion protein. More preferably in the case of cytoplasmic fusion proteins, the method includes releasing the fusion protein from the host cell by a method such as sonication or homogenation. The fusion protein is the purified by conventional means. In still another embodiment, if a secretory leader is employed in the fusion protein construct, the fusion protein can be recovered from a periplasmic extract or from the cell culture medium (using osmotic shock to release the protein). As yet a further step in the above methods, the desired heterologous protein can be cleaved from fusion with the carrier protein by conventional means.

Other aspects and advantages of the present invention will be apparent upon consideration of the following detailed description of preferred embodiments.

In particular, the objective of the present invention is to improve the purification process of recombinant fusion proteins by avoiding the initial expression of these fusion proteins in E. coli as insoluble inclusion bodies by using E. coli carrier proteins having predicted solubility probabilities of at least 90%.

DESCRIPTION OF THE INVENTION

The methods and compositions of the present invention permit the production of large amounts of heterologous peptides or proteins in a stable, soluble form in certain host cells which normally express limited amounts of such soluble peptides or proteins. The present invention produces fusion proteins which retain the desirable characteristics of a carrier protein (i.e., stability, solubility, and a high level of expression).

According to the present invention, the DNA sequence encoding a heterologous (target) peptide or protein selected for expression in a recombinant system is desirably fused directly or indirectly to a DNA sequence encoding a carrier protein as defined herein for expression in the host cell.

This invention is directed toward improving the process of producing proteins by recombinant DNA technology in bacteria, either in the laboratory or in larger scale facilities. The invention would be very useful for the production of those heterologous proteins in bacteria that are normally insoluble when expressed in the bacteria. This invention could be used by laboratory researchers in biotechnology who need to express recombinant proteins substantially in soluble form in bacterial cells. The invention could also be used in large scale industrial processes for the efficient production of recombinant proteins that are generally insoluble when expressed by themselves in bacteria.

The selection of a carrier protein for the fusion protein which results in a more soluble fusion protein is based upon a revised version of the quantitative model developed by Wilkinson and Harrison (1991), for prediction of the solubility of recombinant proteins expressed in $E.$ $coli$ at 37° C. This model, which was based on data in the literature on 81 proteins expressed in $E.$ $coli$, showed that the probability of a given protein being soluble is primarily dependent upon two parameters: fraction of turn-forming residues (Pro, Asp, Gly, and Ser), and the absolute value of the charge average minus 0.03.

The revised Wilkinson-Harrison solubility model involves calculating a canonical variable (CV) or composite parameter for the protein for which solubility is being predicted. The two-parameter model is defined as:

$$CV = \lambda_1 \left( \frac{N+G+P+S}{n} \right) + \lambda_2 \left| \frac{(R+K)-(D+E)}{n} - 0.03 \right| \quad (I)$$

where n=number of amino acids in the protein;

N, G, P, S=number of residues of Asn, Gly, Pro, or Ser, respectively;

R, K, D, E=number of residues of Arg, Lys, Asp, or Glu, respectively;

$\gamma_1 = 15.43$; and $\gamma_2 = -29.56$.

Figure 1:
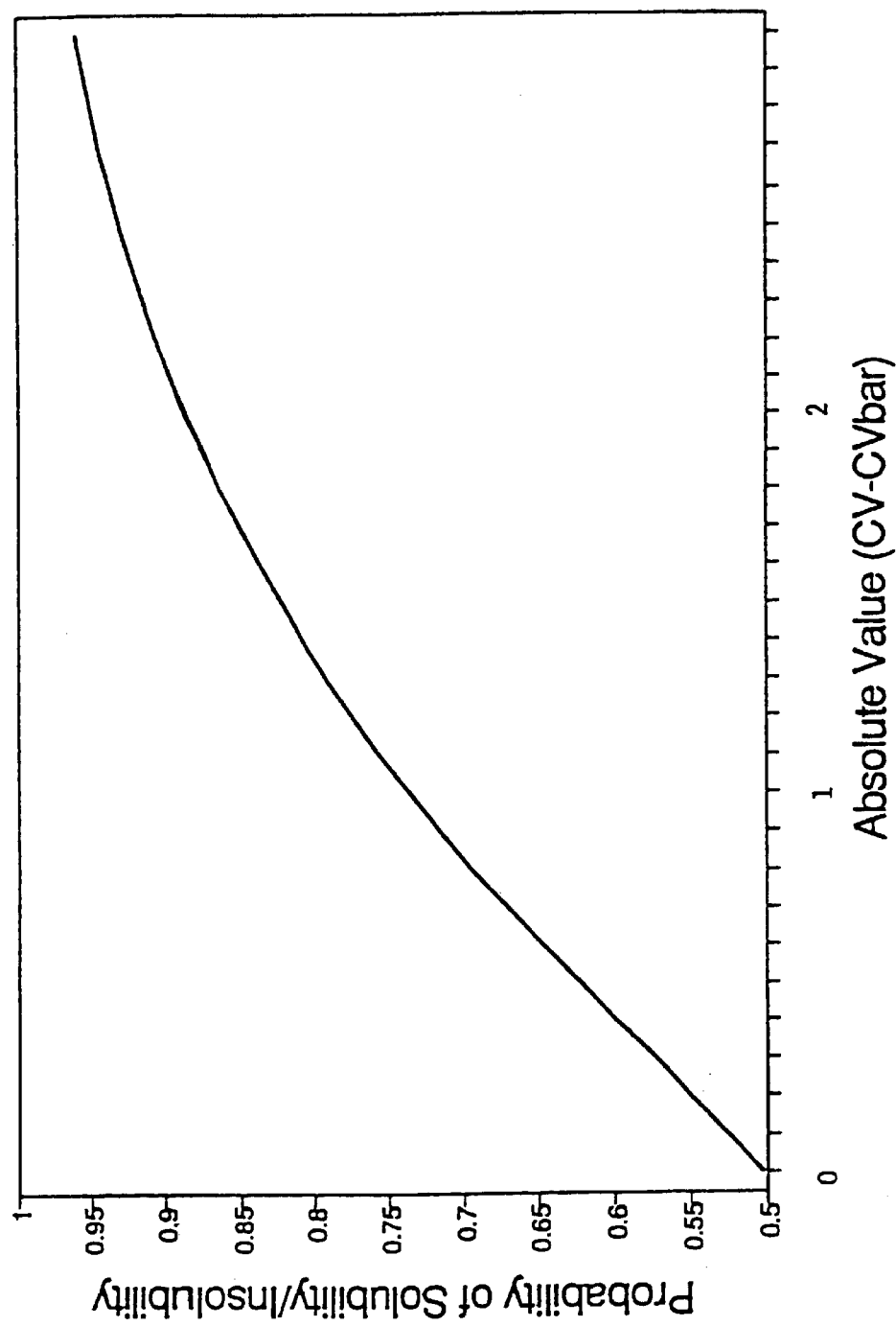
FIG. 1 is a graphical representation of the prediction of protein solubility probability in E. coli from $CV-CV_{bar}$. If $CV-CV_{bar}$ is positive, the protein is predicted to be insoluble. If $CV-CV_{bar}$ is negative, the protein is predicted to be soluble.

The probability of the protein being soluble is determined based on the parameter $CV-CV_{bar}$, where $CV_{bar}$ is the discriminant, equal to 1.71. If $CV-CV_{bar}$ is positive, the protein is predicted to be insoluble, while if $CV-CV_{bar}$ is negative, the protein is predicted to be soluble. The probability of solubility or insolubility can be determined from $CV-CV_{bar}$ using the graph in FIG. 1 or from the following equation:

$$\text{Probability of Solubility or Insolubility} = 0.4934 + 0.276|CV-CV_{bar}| - 0.0392(CV-CV_{bar})^2 \quad (II)$$

Four $E.$ $coli$ proteins, NusA protein, GrpE protein, bacterioferritin (BFR) and 2X-YjgD protein (two YjgD proteins connected at the carboxy terminus of one and at the amino terminus of the other), were selected for further study for use as carrier proteins based upon the new two-parameter version of this model. The properties of fusion proteins comprising carrier proteins of the present invention were compared with thioredoxin alone and as a fusion protein as shown in Table 1.

TABLE 1

Predicted Solubilities of Carrier, Target Proteins, and Carrier/Target Fusion Proteins. The carrier proteins have relatively high solubility probabilites while the target proteins (hIL-3, bGH, and hIFN-γ) do not.

|  | MW (kDA) | Amino Acid Length | Probabilty of Solubility or Insolubility* |
|---|---|---|---|
| Protein |  |  |  |
| 2X-YjgD | 31.2 | 276 | >97% soluble |
| NusA | 55.0 | 495 | 95% soluble |
| BFR | 18.5 | 158 | 95% soluble |
| GrpE | 21.7 | 197 | 92% soluble |
| thioredoxin | 11.7 | 109 | 73% soluble |
| hIL-3 | 15.1 | 133 | 73% insoluble |
| bGH | 21.6 | 189 | 85% insoluble |
| hIFN-γ | 17.1 | 146 | 96% insoluble |
| Fusion Protein |  |  |  |
| 2X-YjgD/hIL-3 | 47.3 | 417 | >97% soluble |
| NusA/hIL-3 | 70.6 | 634 | 86% soluble |
| NusA/bGH | 77.4 | 690 | 80% soluble |
| NusA/hIFNγ | 72.7 | 647 | 79% soluble |
| GrpE/hIL-3 | 37.3 | 336 | 72% soluble |
| BFR/hIL-3 | 34.1 | 297 | 72% soluble |
| thio/hIL-3 | 26.8 | 248 | 54% insoluble |

Note: the ILe-Glu-Gly-Arg sequence for factor Xa cleavage and the amino acids Thr-Gly created by an AgeI restriction site are included in the MW and solubility calculations.
*See Equations I and II Thus, each of the four selected proteins alone or as a fusion protein are predicted to be more soluble than thioredoxin when expressed in $E.$ $coli$ at 37° C.

All $E.$ $coli$ proteins that are predicted by the model to have 90% or greater probability of being soluble and which comprise at least 100 amino acids are within the class of carrier proteins which are contemplated as falling within the present invention.

Examples are shown in Table 2.

TABLE 2

*Escherichia coli* proteins of 100 amino acids or greater in length in the SWISS-PROT protein databank which have a calculated CV-CVbar value of −2.10 or less, which are predicted by the two parameter solubility model of Wilkinson and Harrison to have a solubility probability of 90% or greater when expressed in the *E. coli* cytoplasm.

| SWISS-PROT Protein Name | Total No. of Amino Acids | CV-CV$_{bar}$ | Amino Acids used for CV-CV$_{bar}$ calculation ||||||||
|---|---|---|---|---|---|---|---|---|---|---|
| | | | Arg | Asn | Asp | Glu | Gly | Lys | Pro | Ser |
| RPSD_ECOLI | 613 | −2.48 | 46 | 19 | 54 | 71 | 24 | 34 | 19 | 29 |
| FTSY_ECOLI | 497 | −3.15 | 18 | 11 | 22 | 79 | 30 | 33 | 22 | 15 |
| AMY2_ECOLI | 495 | −2.17 | 20 | 21 | 44 | 40 | 40 | 20 | 23 | 14 |
| NUSA_ECOLI | 495 | −2.62 | 33 | 19 | 42 | 56 | 28 | 25 | 14 | 15 |
| YRFI_ECOLI | 294 | −2.67 | 12 | 16 | 23 | 26 | 19 | 7 | 14 | 7 |
| MAZG_ECOLI | 263 | −3.03 | 21 | 7 | 21 | 32 | 10 | 12 | 7 | 7 |
| S3AD_ECOLI | 263 | −2.38 | 16 | 5 | 18 | 27 | 13 | 8 | 14 | 12 |
| SSEB_ECOLI | 261 | −2.24 | 9 | 6 | 12 | 34 | 17 | 13 | 15 | 14 |
| YCHA_ECOLI | 252 | −2.42 | 13 | 11 | 18 | 26 | 9 | 8 | 12 | 15 |
| YAGJ_ECOLI | 243 | −2.26 | 14 | 5 | 19 | 26 | 12 | 15 | 9 | 10 |
| YFBN_ECOLI | 238 | −2.65 | 15 | 10 | 19 | 23 | 9 | 13 | 4 | 3 |
| NARJ_ECOLI | 236 | −2.44 | 13 | 4 | 19 | 19 | 11 | 8 | 9 | 11 |
| NARW_ECOLI | 231 | −2.36 | 13 | 6 | 21 | 20 | 11 | 9 | 10 | 13 |
| YECA_ECOLI | 221 | −2.54 | 8 | 6 | 13 | 28 | 12 | 11 | 14 | 11 |
| CHEZ_ECOLI | 214 | −2.49 | 14 | 5 | 22 | 15 | 7 | 6 | 9 | 13 |
| GRPE_ECOLI | 197 | −2.34 | 11 | 8 | 13 | 26 | 8 | 13 | 9 | 7 |
| SLYD_ECOLI | 196 | −2.98 | 4 | 6 | 19 | 17 | 29 | 6 | 5 | 5 |
| YJAG_ECOLI | 196 | −3.33 | 11 | 5 | 12 | 25 | 9 | 6 | 5 | 10 |
| YIEJ_ECOLI | 195 | −2.77 | 6 | 6 | 16 | 21 | 17 | 10 | 8 | 7 |
| YGFB_ECOLI | 194 | −3.22 | 4 | 8 | 18 | 16 | 17 | 4 | 9 | 8 |
| YJDC_ECOLI | 191 | −2.13 | 15 | 4 | 15 | 15 | 7 | 6 | 7 | 5 |
| YCDY_ECOLI | 184 | −3.12 | 9 | 3 | 12 | 21 | 8 | 3 | 11 | 12 |
| AADB_ECOLI | 177 | −2.65 | 13 | 2 | 13 | 20 | 14 | 4 | 9 | 5 |
| FLAV_ECOLI | 175 | −4.09 | 4 | 4 | 20 | 17 | 15 | 9 | 5 | 5 |
| FLAW_ECOLI | 173 | −3.32 | 2 | 5 | 16 | 16 | 16 | 8 | 6 | 7 |
| YCED_ECOLI | 173 | −2.57 | 7 | 4 | 12 | 19 | 5 | 8 | 12 | 10 |
| YFHE_ECOLI | 171 | −2.62 | 13 | 2 | 14 | 16 | 3 | 8 | 3 | 9 |
| ASR_ECOLI | 169 | −2.62 | 14 | 8 | 0 | 5 | 5 | 18 | 10 | 9 |
| YGGD_ECOLI | 169 | −2.76 | 4 | 6 | 17 | 9 | 5 | 8 | 5 | 9 |
| YHBS_ECOLI | 167 | −2.39 | 11 | 3 | 15 | 13 | 16 | 2 | 6 | 6 |
| FTN_ECOLI | 165 | −2.21 | 4 | 8 | 7 | 19 | 5 | 9 | 4 | 12 |
| MENG_ECOLI | 161 | −2.44 | 8 | 7 | 15 | 14 | 21 | 2 | 3 | 7 |
| YBEL_ECOLI | 160 | −2.13 | 14 | 4 | 9 | 22 | 7 | 7 | 5 | 8 |
| BFR_ECOLI | 158 | −2.68 | 9 | 10 | 14 | 18 | 11 | 9 | 1 | 4 |
| SMG_ECOLI | 157 | −5.53 | 7 | 6 | 12 | 23 | 5 | 3 | 4 | 3 |
| HYCI_ECOLI | 156 | −2.55 | 5 | 7 | 14 | 13 | 16 | 4 | 10 | 2 |
| SECB_ECOLI | 155 | −2.18 | 4 | 7 | 8 | 13 | 9 | 3 | 7 | 8 |
| YBEY_ECOLI | 155 | −4.29 | 3 | 4 | 9 | 23 | 8 | 5 | 8 | 9 |
| ELAA_ECOLI | 153 | −2.39 | 6 | 4 | 12 | 12 | 10 | 5 | 6 | 7 |
| YFJX_ECOLI | 152 | −2.37 | 6 | 5 | 11 | 11 | 11 | 1 | 7 | 8 |
| MIOC_ECOLI | 146 | −2.23 | 2 | 4 | 10 | 16 | 15 | 7 | 7 | 10 |
| YJGD_ECOLI | 138 | −9.37 | 3 | 3 | 22 | 25 | 8 | 3 | 4 | 3 |
| HYFJ_ECOLI | 137 | −2.51 | 7 | 1 | 7 | 13 | 5 | 4 | 4 | 8 |
| RL16_ECOLI | 136 | −2.45 | 14 | 2 | 3 | 7 | 13 | 16 | 7 | 2 |
| RS6_ECOLI | 135 | −3.17 | 12 | 4 | 10 | 20 | 5 | 6 | 5 | 4 |
| YHHG_ECOLI | 133 | −2.17 | 10 | 3 | 14 | 7 | 7 | 3 | 1 | 8 |
| GCSH_ECOLI | 129 | −4.06 | 1 | 3 | 11 | 17 | 8 | 6 | 5 | 12 |
| TRD5_ECOLI | 129 | −4.88 | 6 | 3 | 16 | 15 | 8 | 2 | 10 | 4 |
| MSYB_ECOLI | 124 | −8.22 | 4 | 4 | 14 | 24 | 8 | 1 | 4 | 2 |
| RS12_ECOLI | 123 | −2.23 | 15 | 5 | 3 | 4 | 11 | 13 | 7 | 6 |
| RL7_ECOLI | 120 | −2.38 | 1 | 1 | 6 | 16 | 8 | 13 | 2 | 6 |
| YACL_ECOLI | 120 | −3.85 | 6 | 5 | 7 | 18 | 9 | 4 | 0 | 5 |
| YBFG_ECOLI | 120 | −3.11 | 5 | 3 | 8 | 12 | 7 | 3 | 3 | 6 |
| RL20_ECOLI | 117 | −5.17 | 16 | 3 | 4 | 2 | 6 | 14 | 0 | 4 |
| HYPA_ECOLI | 116 | −2.27 | 8 | 0 | 5 | 12 | 7 | 4 | 1 | 4 |
| PTCA_ECOLI | 116 | −2.64 | 3 | 3 | 7 | 12 | 6 | 8 | 1 | 5 |
| YZPK_ECOLI | 115 | −2.76 | 23 | 2 | 2 | 5 | 8 | 3 | 5 | 7 |
| HYBF_ECOLI | 113 | −2.90 | 5 | 0 | 6 | 11 | 5 | 3 | 2 | 8 |
| FER_ECOLI | 110 | −3.41 | 6 | 3 | 9 | 14 | 5 | 3 | 6 | 7 |
| YR7J_ECOLI | 110 | −2.33 | 8 | 2 | 1 | 1 | 4 | 9 | 5 | 7 |
| GLPE_ECOLI | 108 | −2.35 | 3 | 4 | 10 | 5 | 8 | 3 | 3 | 4 |
| YGGL_ECOLI | 108 | −2.23 | 8 | 3 | 8 | 15 | 6 | 8 | 2 | 5 |
| CYAY_ECOLI | 106 | −3.74 | 5 | 4 | 12 | 10 | 9 | 3 | 1 | 5 |
| YEHK_ECOLI | 105 | −2.50 | 11 | 4 | 8 | 14 | 2 | 3 | 6 | 4 |
| YR7G_ECOLI | 105 | −4.14 | 3 | 3 | 13 | 12 | 7 | 4 | 7 | 7 |
| YQFB_ECOLI | 103 | −2.81 | 5 | 2 | 9 | 9 | 5 | 6 | 2 | 3 |
| YCCD_ECOLI | 101 | −2.52 | 8 | 3 | 5 | 10 | 4 | 1 | 3 | 2 |
| RS14_ECOLI | 100 | −2.17 | 14 | 3 | 5 | 5 | 5 | 11 | 4 | 8 |

Preferably, the carrier protein of the present invention has a solubility probability of 90% or greater as determined from the revised Wilkinson-Harrison solubility model, shown herein, wherein the parameter $CV-CV_{bar}$ is negative.

The present invention comprises a method of purifying a heterologous protein wherein the heterologous protein is expressed from a fusion gene comprising a gene encoding the heterologous protein which optionally is linked via a linker gene to a gene encoding a carrier protein as described elsewhere herein. Linker genes are well known to those of ordinary skill in the art. As noted, an example is the linker gene which encodes the Ile-Glu-Gly-Arg linker which is cleaved by Factor $X_a$ protease. Other linkers may be cleaved by trypsin, enterokinase, collagenase and thrombin for example. Other linkers and their linked genes will be readily apparent to those of ordinary skill in the art. Alternatively, the cleavage site in the linker may be a site capable of being cleaved upon exposure to a selected chemical, e.g., cyanogen bromide, hydroxylamine, or low pH.

Figure 2:
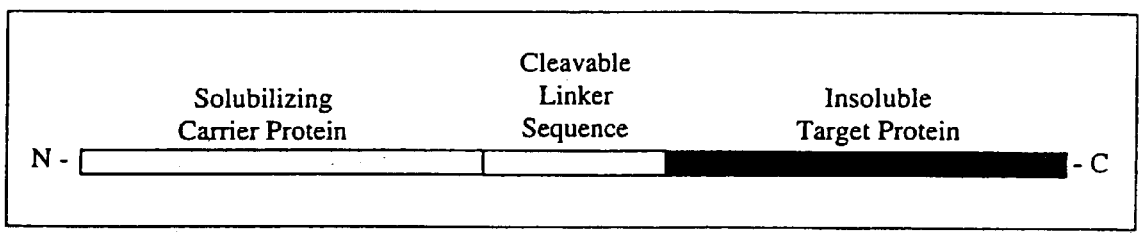
FIG. 2 is a schematic drawing of the fusion protein containing the target protein desired to be solubilized.

A schematic drawing of a fusion protein contemplated by the present invention which contains the carrier protein and the insoluble heterologous protein is shown in FIG. 2. The carrier protein and the target protein are connected by a cleavable linker sequence which can be cleaved by an enzyme to release the target protein. An example of a cleavable linker sequence is, as noted above, Ile-Glu-Gly-Arg, which is cleaved at the carboxy terminus of Arg by Factor $X_a$ protease.

Cleavage at the selected cleavage site enables separation of the heterologous protein or peptide from the fusion protein to yield the mature heterologous peptide or protein. The mature peptide or protein may then be obtained in purified form, free from any polypeptide fragment of the carrier protein to which it was previously linked. The cleavage site, if inserted into a linker useful in the fusion sequences of this invention, does not limit this invention. Any desired cleavage site, of which many are known in the art, may be used for this purpose.

The optional linker sequence of a fusion sequence of the present invention may serve as a simple amino acid sequence of a sufficient length to prevent any steric hindrance between the carrier molecule and the selected heterologous peptide or protein.

Whether or not such a linker sequence is necessary will depend upon the structural characteristics of the selected heterologous peptide or protein and whether or not the resulting fusion protein is useful without cleavage. Alternatively, where the mature protein sequence may be naturally cleaved, no linker may be needed.

In one embodiment therefore, the fusion sequence of this invention contains a carrier sequence, as defined herein, fused directly at its amino or carboxyl terminal end to the sequence of the selected peptide or protein. The resulting fusion protein is thus a soluble cytoplasmic fusion protein. In another embodiment, the fusion sequence further comprises a linker sequence interposed between the carrier sequence and the selected peptide or protein sequence. This fusion protein is also produced as a soluble cytoplasmic protein. The cytoplasmic fusion protein can be purified by conventional means.

The present invention comprises a method of producing and purifying a heterologous protein in *E. coli*. An *E. coli* transformed with recombinant plasmid comprising a gene for a fusion protein is grown at a suitable temperature. Suitable temperatures may be in a range of from about 20° C. to about 40° C., more preferably, the range is about 23° C. to about 38° C., still more preferably, from about 30° C. to about 37° C., and still more preferably from about 35° C. to about 37° C.

The cells are induced to produce the fusion protein and the cells are harvested and treated to obtain the fraction containing the soluble fusion protein, which is then treated to isolate the heterologous protein from the carrier protein in a manner well-known to one of ordinary skill in the art. The carrier protein used is one having a solubility probability of 90% or greater as predicted by the two-parameter Wilkinson-Harrison model described herein. The present invention also contemplates that the fusion gene and protein may be made up of more than one carrier protein gene or carrier protein, including more than one copy of a carrier or more than one specific type of carrier.

In an especially preferred version of the invention, the entire fusion protein expressed in the induced *E. coli* has a predicted solubility probability of 65% or greater as determined by the two-parameter Wilkinson-Harrison model described herein. More preferably the entire fusion protein has a solubility probability of 75% or greater, and even more preferably has a solubility probability of 90% or greater and thus the fusion protein is substantially soluble, that is it is at least 65%, 75% or most preferably at least 90% soluble.

Where used herein the term carrier protein is also meant to include alternate versions of the carrier protein which comprise substitutions or deletions of amino acid residues which are not critical or required for the normal folding of the protein such that the alternate versions still have a solubility probability of 90% or greater.

The present invention is also directed to a method of obtaining expression in soluble form of a recombinant protein by the separate co-expression of NusA protein and the heterologous protein in the cell. One way to co-express NusA is to transform *E. coli* cells with two plasmids, one that comprises the gene for NusA protein and the other that comprises the gene for a heterologous protein whose soluble expression is desired (e.g., hIL-3). Both proteins are induced so that both NusA and the desired protein are produced in the cytoplasm of *E. coli*.

Solubility of the desired protein is higher in cells with overexpression of the NusA gene than in cells without overexpression of the NusA gene. NusA appears to cause an increase in solubility of the desired protein due to its transcriptional pausing activity. It is anticipated that other proteins which cause transcriptional pausing will also be effective in causing an increase in the solubility of expressed proteins. In this regard, the present invention comprises a method of increasing solubility of expressed proteins by expressing the genes in an expression system such as *E. coli* comprising the NusA gene, or other gene, which encodes a protein which has transcriptional pausing activity.

DNA sequences which hybridize to the sequences for *E. coli* carrier proteins defined herein under either stringent or relaxed hybridization conditions also encode carrier proteins for use in this invention. An example of one such stringent hybridization condition is hybridization at 4×SSC at 65° C., followed by a washing in 0.1×SSC at 65° C. for an hour. Alternatively, an exemplary stringent hybridization condition is in 50% formamide, 4×SSC at 42° C. Examples of non-stringent hybridization conditions are 4×SSC at 50° C. with 30–40% formamide at 42° C. The use of all such carrier protein sequences are believed to be encompassed in this invention.

Construction of a fusion sequence of the present invention, which comprises the DNA sequence of a selected heterologous peptide or protein and the DNA sequence of a carrier protein sequence, as defined herein, employs convention genetic engineering techniques [see, Sambrook et al., *Molecular Cloning. A Laboratory Manual,* Cold Spring Harbor Laboratory, Cold Spring Harbor, N.Y. (1989)]. Fusion sequences may be prepared in a number of different ways. For example, the selected heterologous protein may be fused to the amino terminus of the carrier molecule. Alternatively, the selected protein sequence may be fused to the carboxyl terminus of the carrier molecule.

This fusion of a desired heterologous peptide or protein to the carrier protein increases the solubility of the heterologous peptide or protein. At either the amino or carboxyl terminus, the desired heterologous peptide or protein is fused in such a manner that the fusion does not destabilize the native structure of either protein. Furthermore, more than one copy of the DNA coding sequence of the carrier protein (e.g., at lest two or more) may be used in the fusion gene for increasing solubility of the resulting fusion protein.

This invention is not limited to any specific type of heterologous peptide or protein. A wide variety of heterologous (i.e., foreign in reference to the host genome) genes or gene fragments are useful in forming the fusion sequences of the present invention. Any selected, desired DNA sequence could be used. While the compositions and methods of this invention are most useful for peptides or proteins which are not expressed, expressed in inclusion bodies, or expressed in very small amounts in bacterial and yeast hosts, the selected heterologous peptides or proteins can include any peptide or protein useful for human or veterinary therapy, diagnostic or research applications in any expression system. For example, hormones, cytokines, growth or inhibitory factors, enzymes, modified or wholly synthetic proteins or peptides can be produced according to this invention in bacterial, yeast, mammalian or other eukaryotic cells and expression systems suitable therefor. However, especially preferred embodiments of the invention comprise heterologous proteins and genes thereof which are not produced in soluble form at normal growth temperatures (e.g., 37° C.) when fused to thioredoxin, maltose-binding protein, or glutathione s-transferase for example.

A variety of DNA molecules incorporating the above-described fusion sequences may be constructed for expressing the selected heterologous peptide or protein according to this invention. At a minimum, a desirable DNA sequence according to this invention comprises a fusion sequence described above, in association with, and under the control of, an expression control sequence capable of directing the expression of the fusion protein in a desired host cell. For example, where the host cell is an *E. coli* strain, the DNA molecule desirably contains a promoter which functions in *E. coli*, a ribosome binding site, and optionally, a selectable marker gene and an origin of replication if the DNA molecule is extra-chromosomal. Numerous bacterial expression vectors containing these components are known in the art for bacterial expression, and can easily be constructed by standard molecular biology techniques. Similarly known yeast and mammalian cell vectors and vector components may be utilized where the host cell is a yeast cell or a mammalian cell.

The DNA molecules containing the fusion sequences may be further modified to contain different codons to optimize expression in the selected host cell, as is known in the art.

These DNA molecules may additionally contain multiple copies of the carrier protein-encoding DNA sequence, with the gene encoding the heterologous protein fused to only one of the repeated carrier DNA sequences, or with the gene encoding the heterologous protein fused to all copies of the DNA of the carrier such that the resulting fusion protein comprises two or more copies of the carrier protein.

In an alternative version of the invention, more than one type of carrier protein of the type contemplated herein may be used in a single fusion protein, wherein the fusion protein is encoded by at least two different genes each encoding a different carrier protein.

Host cells suitable for the present invention are preferably bacterial cells. For example, the various strains of *E. coli* (e.g., HB101, NN522, JM109, W3110, and the JM105 strain used in the following examples) are well-known as-host cells in the field of biotechnology.

To produce the fusion protein of this invention, the host cell is either transformed with, or has integrated into its genome, a DNA molecule comprising a DNA sequence encoding a carrier protein fused to the DNA sequence of a selected heterologous peptide or protein under the control of an expression control sequence capable of directing the expression of a fusion protein. The host cell is then cultured under known conditions suitable for fusion protein production. If the fusion protein accumulates in the cytoplasm of the cell it may be released by conventional bacterial cell lysis techniques and purified by conventional procedures including selective precipitations and column chromatographic methods. If a secretory leader is incorporated into the fusion molecule substantial purification is achieved when the fusion protein is secreted into the periplasmic space or the growth medium.

A protein secreted into the periplasmic space may be selectively released from the cell by osmotic shock or freeze/thaw procedures. Although final purification is still required for most purposes, the initial purity of fusion proteins in preparations resulting from these procedures is generally superior to that obtained in conventional whole cell lysates, reducing the number of subsequent purification steps required to attain homogeneity. In a typical osmotic shock procedure, the packed cells containing the fusion protein are resuspended on ice in a buffer containing EDTA and having a high osmolarity, usually due to the inclusion of a solute, such as 20% w/v sucrose, in the buffer which cannot readily cross the cytoplasmic membrane. During a brief incubation on ice the cells plasmolyze as water leaves the cytoplasm down the osmotic gradient. The cells are then switched into a buffer of low osmolarity, and during the osmotic re-equilibration the contents of the periplasm are released to the exterior. A simple centrifugation following this release removes the majority of bacterial cell-derived contaminants from the fusion protein preparation. Alternatively, in a freeze/thaw procedure the packed cells containing the fusion protein are first suspended in a buffer containing EDTA and are then frozen. Fusion protein release is subsequently achieved by allowing the frozen cell suspension to thaw. The majority of contaminants can be removed as described above by a centrifugation step. The fusion protein is further purified by well-known conventional methods.

The resulting fusion protein is stable and soluble, often with the heterologous peptide or protein retaining its bioactivity. The heterologous peptide or protein may optionally be separated from the carrier protein by cleavage, as discussed elsewhere herein.

The production of fusion proteins according to this invention reliably improves solubility of desired heterologous proteins and enhances their stability to proteases in the expression system. This invention also enables high level expression of certain desirable therapeutic proteins, which are otherwise produced at low levels in bacterial host cells.

The following examples illustrate embodiments of the present invention, but are not intended to limit the scope of the disclosure.

EXAMPLES

As noted above, four carrier proteins (NusA, GrpE, BFR, and YjgD-2 copies) were tested. Genes for fusion proteins were constructed in expression plasmid pKK223-3 (Pharmacia Biotech) downstream of the tac promoter. *E. coli* strain JM105 was transformed with the recombinant plasmids, and the fusion proteins were expressed by induction of the cells growing at 37° C. by the addition of 1 mM isopropyl-β-D-thiogalactoside (IPTG). The cells were harvested 3 hours from the start of induction. The cells were sonicated after harvesting to break the cell walls, and the cell solids material was separated by centrifugation. Construction of such plasmids and transformed strains comprising other carrier proteins and target proteins and growth thereof is considered to be within the skill of a person of ordinary skill in the art and therefore it is not considered necessary to provide further methodological details.

All of the carrier proteins (NusA, GrpE, 2X-YjgD and BFR) were tested with human interleukin-3 (hIL-3) as the heterologous protein. hIL-3 previously has been found to be expressed in solid form in "inclusion bodies" in *E. coli* (Donahue et al., 1988; Lutsenko, 1992). hIL-3 has a molecular weight of 15.1 kilodaltons and is predicted to be insoluble by the revised Wilkinson-Harrison solubility model (see Table 1). The NusA carrier protein was additionally tested in fusion proteins with bovine growth hormone (bGH) and human interferon-γ (hIFN-γ). Both bGH and hIFN-γ were previously expressed in inclusion bodies in *E. coli* at 37° C. (George et al., 1985; Haelewyn and De Ley, 1995). bGH and hIFN-γ have molecular weights of 21.6 kilodaltons and 17.1 kilodaltons, respectively, and are both predicted to be insoluble by the revised Wilkinson-Harrison solubility model (Table 1). For convenience, the linker Ile-Glu-Gly-Arg was used to link the carrier protein to the heterologous protein in all of the fusion proteins studied.

Both the cell insoluble material and the clarified supernatant were analyzed for proteins by sodium dodecyl sulfate-polyacrylamide gel electrophoresis (SDS-PAGE). Equal portions of cell lysate, soluble fraction, and insoluble fraction were loaded onto the gel. The SDS-PAGE results are shown in FIGS. 3 and 4.

Figure 3:
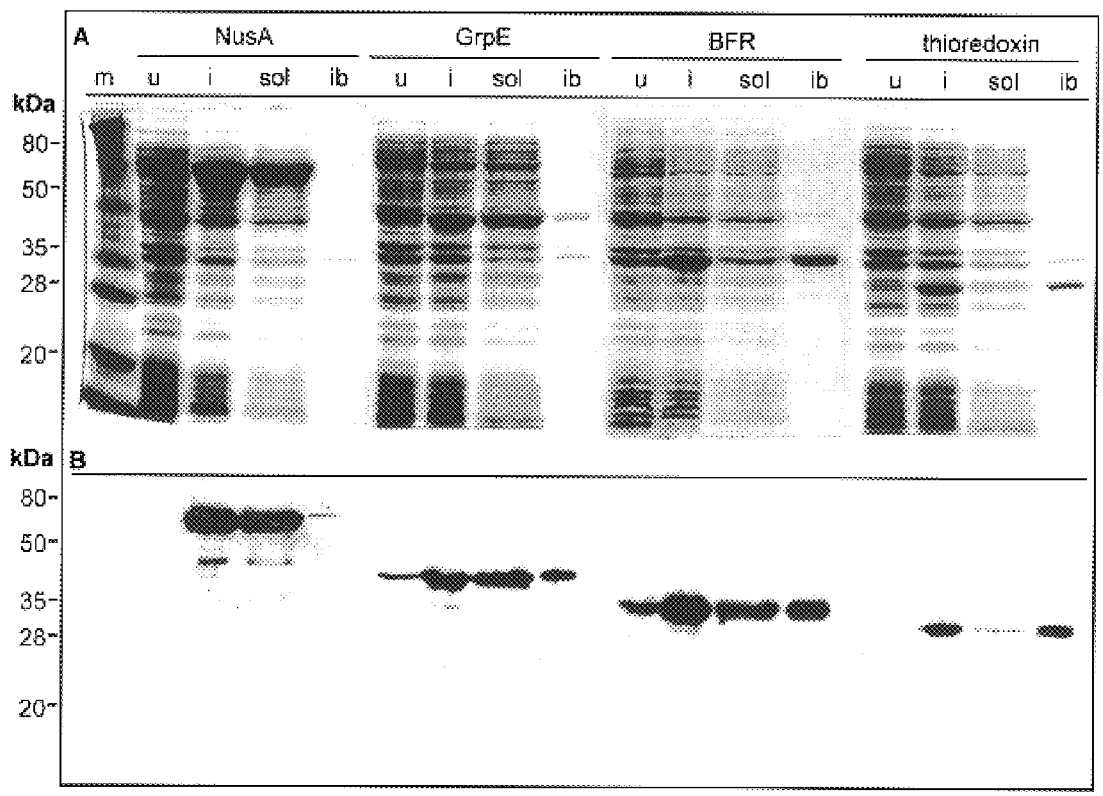
FIGS. 3A–3B, (A) is an SDS-PAGE and (B) is a western blot of soluble and insoluble cell fractions for fusion proteins comprising NusA, GrpE, BFR and thioredoxin as carrier proteins and hIL-3 as the heterologous protein.

FIG. 3 shows NusA, GrpE, BFR, and thioredoxin fusion proteins containing hIL-3. Equal portions of cell lysate, soluble fraction, and insoluble fraction were loaded. Column (m) represents markers, (u)—the uninduced whole cell lysate, (i)—the induced whole cell lysate, (sol)—the soluble fraction, and (ib)—the inclusion body fraction. Fusion proteins were expressed from plasmid pKK223-3 under control of the tac promoter in *E. coli* JM105 at 37° C. Cells were induced with 1 mM IPTG and grown for 3 h post-induction. The western blot was probed with mouse anti-hIL-3 monoclonal antibody and visualized using chemiluminescence. Percentage solubility is based on the western blots (density of soluble band divided by the density of the soluble plus insoluble bands).

Figure 4:
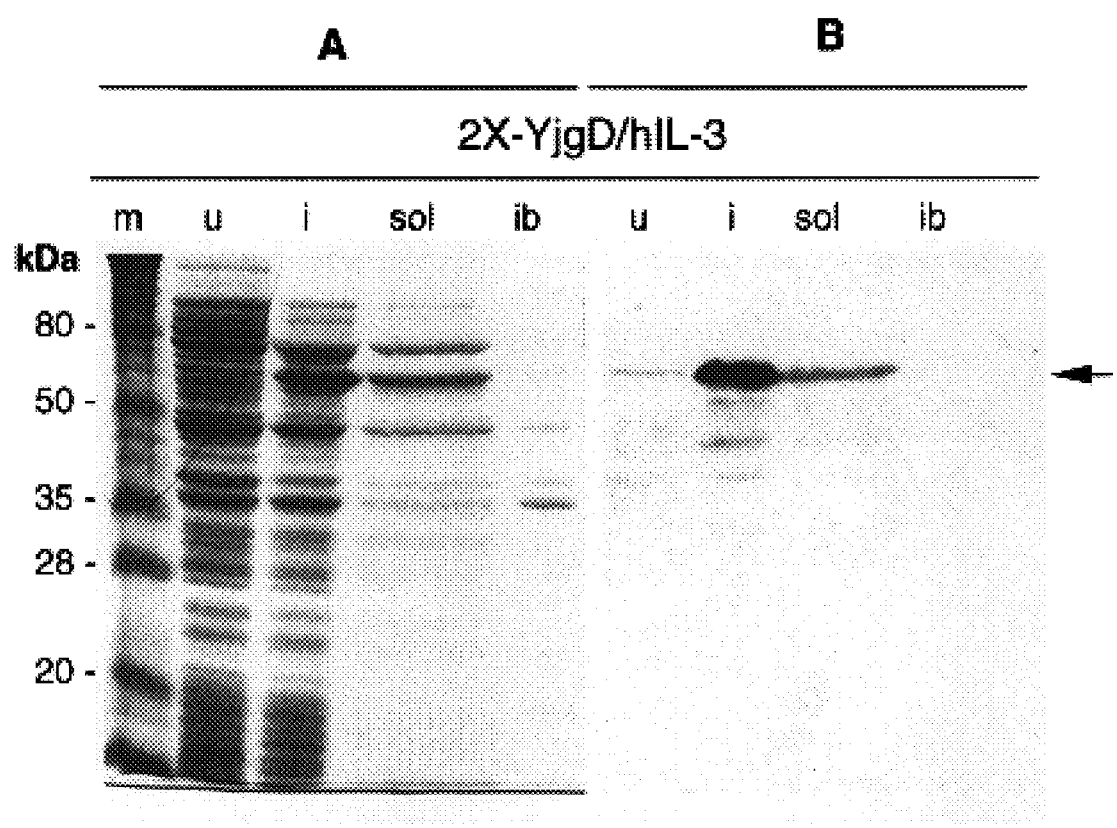
FIGS. 4A–4B are an SDS-PAGE (A) and western blot (B) of soluble and insoluble fractions of 2x-YjgD/hIL-3 clones.

FIG. 4 shows SDS-PAGE of soluble and insoluble cell fractions for 2X-YjgD/hIL-3 clones. SDS-PAGE (A) and western blot (B) of 2X-YjgD/hIL-3 fusion protein. Equal portions of cell lysate, soluble fraction, and insoluble fraction were loaded. Column (m) represents markers, column (u) represents uninduced whole cell lysate, column (1) represents induced whole cell lysate, column (sol) represents soluble fraction, and column (ib) represents inclusion body fraction. Fusion proteins were expressed from plasmid pKK223-3 under control of the tac promoter in *E. coli* JM105 at 37° C. Cells were induced with 1 mM IPTG and grown for 3 h post-induction. The western blot was probed with mouse anti-hIL-3 monoclonal antibody and visualized using chemiluminescence.

These results indicate that the NusA/hIL-3, GrpE/hIL-3, BFR-/hIL-3, and 2X-YjgD/hIL-3 fusion proteins were expressed substantially in the soluble fraction (97%, 71%, 47% and 100%, respectively), while the thioredoxin/hIL-3 fusion protein was expressed primarily in the insoluble fraction (8% solubility). It is noteworthy that the level of expression of the NusA/hIL-3 fusion protein is much higher than for the other fusion proteins. Two YjgD proteins were linked together in the 2X-YjgD/hIL-3 fusion protein because it was found that when only one YjgD protein was used, the YjgD/hIL-3 fusion protein was mostly insoluble. Two or more copies of the solubilizing protein may be used in the present invention where a single copy does not result in substantial solubilization of the fusion protein. The YjgD protein is advantageous to use in a fusion protein since it is a highly acidic protein (isoelectric point, or pI, of 3.6) and thus could be conveniently and economically purified by ion exchange chromatography.

Figure 5:
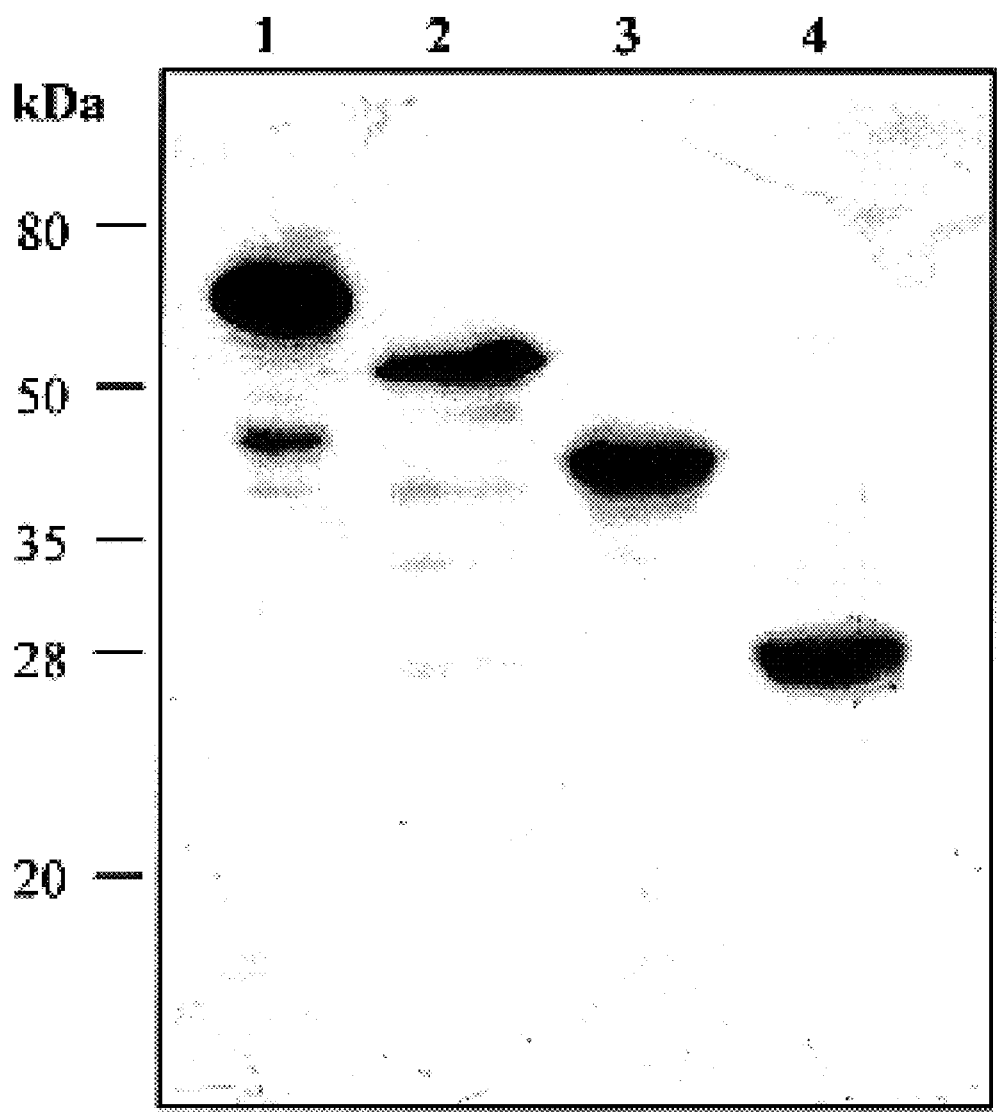
FIG. 5 is a western blot of whole cell induced cultures expressing hIL-3 fusion proteins with NusA, 2x-YjgD, GrpE and thioredoxin carrier proteins.

FIG. 5 shows a western blot of whole cell induced cultures expressing hIL-3 fusion proteins with NusA, 2X-YjgD, GrpE, and thioredoxin. Positions of prestained molecular weight markers are shown at left. Lane 1, NusA/hIL-3. Lane 2, 2X-YjgD/hIL-3. Lane 3, GrpE/hIL-3. Lane 4, thioredoxin/hIL-3. The blot was probed with a mouse monoclonal antibody that neutralizes hIL-3 activity and was visualized using chemiluminescence. Fusion proteins were expressed from plasmid pKK223-3 under control of the tac promoter in *E. coli* JM105 at 37° C. Cells were induced with 1 mM IPTG and grown for 3 h post-induction.

The blot was probed with mouse anti-hIL-3 monoclonal antibody and visualized using chemiluminescence. These results show that the hIL-3 reactivity is at the molecular weight position for the corresponding fusion protein, indicating that each fusion protein contains hIL-3. The hIL-3 reactivity is significantly larger and denser for the NusA/hIL-3 fusion protein than for the other fusion proteins, which indicates that more hIL-3 is being expressed in the NusA/hIL-3 fusion than in the other fusions. The small band between 35 and 50 kDa for NusA/hIL-3 indicates that a slight amount of cleavage of this fusion protein could be occurring.

Table 3 shows the biological activity of hIL-3 in several fusion proteins. In order to determine if the hIL-3 present in each of the fusion proteins was biologically active, indicating that hIL-3 was properly folded, a cell proliferation assay was performed on each fusion protein in the crude cell lysates (Table 3). hIL-3 activity was found to be present in all fusion proteins with the highest amount of native activity present in the NusA/hIL-3 protein. It should be noted that reductions in native activity are most likely due to the presence of the carrier protein, which may interfere with the receptor binding properties of hIL-3. hIL-3 cell proliferation assays using a TF-1 cell line were performed by Dr. Robert House at the Illinois Institute of Technology Research Institute (Chicago).

TABLE 3

Activity of Recombinant Human Interleukin-3. The activity of hIL-3 was determined in the soluble crude cell lysates of various fusion protein constructs.

| hIL-3 Fusion Protein | hIL-3 (μg/ml) Est. by SDS-PAGE and BCA Total Protein Assay | hIL-3 (μg/ml) Cell Proliferation Assay | Percent Native Activity |
|---|---|---|---|
| NusA/hIL-3 | 7.5 | 5.0 | 67 |
| GrpE/hIL-3 | 5.2 | 0.3 | 6 |
| BFR/hIL-3* | 8.7 | 1.0 | 12 |
| Thioredoxin/hIL-3* | 7.5 | 3.6 | 48 |

*Expressed at 23° C. to ensure adequate levels of hIL-3 for the cell proliferation assay. All other fusion proteins were grown at 37° C.

Figure 6:
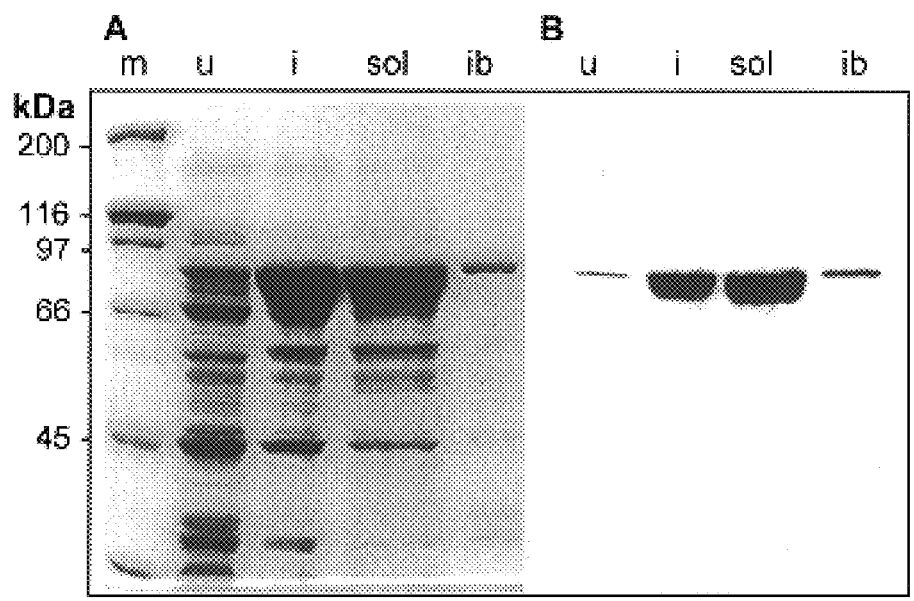
FIGS. 6A–6B (A) is an SDS-PAGE and (B) is a western blot of bovine growth hormone (bGH) expressed as a fusion to NusA.
Figure 7:
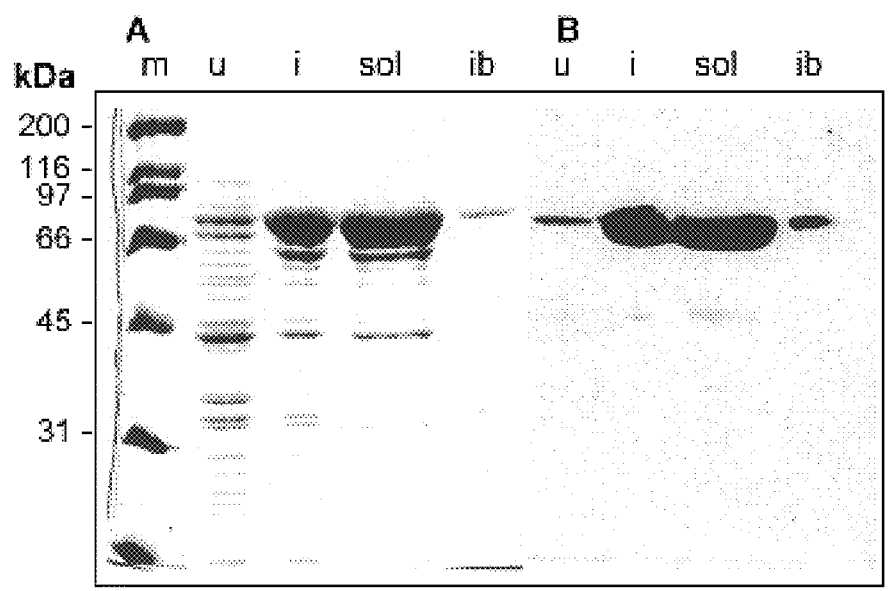
FIGS. 7A–7B (A) is an SDS-PAGE and (B) is a western blot of human interferon-γ (hIFN-γ) expressed as a fusion to NusA.

The SDS-PAGE and western blotting results for the NusA/bGH and NusA/IFN-γ fusion proteins in the cell lysate, the soluble fraction, and the insoluble fraction are shown in FIGS. 6 and 7, respectively.

FIG. 6 shows (A) an SDS-Page and (B) a western blot of bovine growth hormone (bGH) expressed as a fusion to NusA. Equal portions of cell lysate, soluble fraction, and insoluble fraction were loaded. Column (m) indicates molecular weight markers, (u) indicates uninduced, (i) indicates induced, (sol) indicates soluble fraction, and (ib) indicates insoluble fraction. The NusA/bGH fusion protein was expressed from plasmid pKK223-3 under control of the tac promoter in *E. coli* JM105 at 37° C. Cells were induced with 1 mM IPTG and grown for 3 h post induction. The western blot was probed with rabbit anti-bGH polyclonal antibody and visualized using chemiluminescence. The percentage solubility based on the western blot was 89%.

FIG. 7 shows (A) an SDS-PAGE and (B) a western blot of human interferon-γ (hIFN-γ) expressed as a fusion to NusA. Equal portions of cell lysate, soluble fraction, and insoluble fraction were loaded. Column (m) indicates molecular weight markers, (u) indicates uninduced, (i) indicates induced, (sol) indicates soluble fraction, and (ib) indicates insoluble fraction. The NusA/hIFN-γ fusion protein was expressed from plasmid pKK223-3 under control of the tac promoter in *E. coli* JM105 at 37° C. Cells were induced with 1 mM IPTG and grown for 3 h post-induction. The western blot was probed with rabbit anti-hIFN-γ monoclonal antibody and visualized using chemiluminescence. The percentage solubility based on the western blot is 87%.

It can be seen that both of these fusion proteins are almost a completely soluble. The Western blots indicate that the percentage solubilities of the NusA/bGH and NusA/hIFN-γ fusion proteins were 89% and 87%, respectively.

Isolation of the fusion proteins and of the heterologous proteins to complete purity is within the ability of a person of ordinary skill in the art. Therefore it is not deemed necessary to further describe said isolation and purification processes herein.

These results agreed very well with the SDS-PAGE results in FIGS. 3 and 4 for the cell fractions containing overexpressed fusion protein. In addition, Western blots were performed on cell fractions for two other fusions induced at 23° C. for 3 hours: bacterioferritin-IL-3 and YjgD-IL-3. Bacterioferritin (denoted by BFR in Table 2) has a molecular weight of 18.5 kDa, and YjgD has a molecular weight of 15.6 kDa. For both of these fusion proteins, the IL-3 was predominantly in the soluble fraction (the amount in the insoluble fraction was approximately one-fifth of that in the soluble fraction for BFR and 0% for YjgD). Also according to Western blotting results, at 37° C. the bacterioferritin-IL-3 fusion protein was partially soluble (approximately 50% of the total was soluble), compared to very little solubility for the thioredoxin-IL-3 fusion protein at this same temperature.

Bacterioferritin by itself is predicted to have a solubility probability of 95% according to the revised solubility model of Wilkinson and Harrison. Thus, the revised model of Wilkinson and Harrison correctly predicts that bacterioferritin has better solubilizing ability than thioredoxin. Bacterioferritin and NusA have identical predicted solubilities, and it is believed that NusA-IL-3 is more soluble than bacterioferritin-IL-3 at identical induction temperatures because NusA is a considerably larger protein. An advantage of the use of bacterioferritin in fusion proteins is that the cells containing the fusion protein are reddish in color because of the presence of the bacterioferritin. Thus, screening for the presence of bacterioferritin in cells is very simple.

For the fusion proteins disclosed in this invention, expression in *E. coli* in the temperature range of room temperature (20–23° C.) to 40° C. should be considered. The optimal temperature for growth of *E. coli* is 37° C. Expression at temperatures lower than 37° C. will give slower rates of cell growth and protein expression but, in some instances, may give acceptable rates down to room temperature. For example, the bacterioferritin-IL-3 protein provided good expression levels for 3 hours of growth after induction at 23° C.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

REFERENCES CITED

Donahue, R. E., Seehra, J., Metzger, M., Lefebvre, D., Rock, B., Carbone, S., Nathan, D. G., Garnick, M., Sehgal, P. K., Laston, D., LaVallie, E., McCoy, J., Schendel, P., Norton, C., Turner, K., Yang, Y. C., and Clark, S. C. (1988). Human IL-3 and GM-CSF act synergistically in stimulating hematopoiesis in primates. *Science*, 241:1820–1823.

George, H. J., L'Italien, J. J., Pilacinski, W. P., Glassman, D. L., and Krzyzek, R. A. (1985). High-level expression in *Escherichia coli* of biologically active bovine growth hormone. *DNA*, 4:273–281.

Georgiou, G. and Valax, P. (1996). Expression of correctly folded proteins in *Escherichia coli*. *Current Opinion in Biotechnology*, 7:190–197.

Guan, C., Li, P., Riggs, P. D., and Inouye, H. (1988). Vectors that facilitate the expression and purification of foreign peptides in *Escherichia coli* by fusion to maltose-binding protein. *Gene*, 67:21–30.

Haelewyn, J. and De Ley, M. (1995). A rapid single-step purification method for human interferon-γ from isolated *Escherichia coli* inclusion bodies. *Biochemistry and Molecular Biology International*, 37:1163–1171.

LaVallie, E. R., DiBlasio, E. A., Kovacic, S., Grant, K. L., Schendel, P. F., and McCoy, J. M. (1993). A thioredoxin gene fusion expression system that circumvents inclusion body formation in the *E. coli* cytoplasm. *Bio/Technology*, 11:187–193.

Lutsenko, S. V., Gurevich, A. I., Ptitsyn, L. R., Riazanova, L. A., and Smirnov, V. A. (1992). Recombinant interleukin-3 expression in *E. coli*. *Bioorg. Khim.*, 18:391–397.

Smith, D. B. and Johnson, K. S. (1988). Single-step purification of polypeptides expressed in *Escherichia coli* as fusions with glutathione S-transferase. *Gene*, 67:31–40.

Wilkinson, D. L. and Harrison, R. G. (1991). Predicting the solubility of recombinant proteins in *Escherichia coli*. *Bio/Technology*, 11:443–448.22

Crombie, T., Swaffield, J. and Brown, A. (1992). Protein Folding within the Cell Is Influenced by Controlled Rates of Polypeptide Elongation. *J. Mol. Biol.*, 228:7–12.

Kiefhaber, T., Rainer, R., Hans-Helmut, K. and Buchner, J. (1991), Protein Aggregation in vitro and in vivo: A Quantitative Model of the Kinetic Competition Between Folding and Aggregation. *Bio/Technology*, 9:825–829.

Kopetzki, E., Schumacher, G., and Buckel, P. (1989), Control of Formation of Active Soluble or Inactive Insoluble Baker's Yeast α-glucosidase PI in *Escherichia coli* by Induction and Growth Conditions. *Mol. Gen. Genet.*, 216:149–155.

Zhang, Y. and Hanna, M. (1995) Expression and Functional Characterization of *Escherichia coli* NusA and Lambda Q as Glutathione S-Transferase Fusion Proteins. *Protein Exoression and Purification*, 6:625–631.

What is claimed is:

1. A fusion DNA sequence comprising a first DNA sequence encoding a heterologous protein which is normally insoluble when expressed in bacteria and a second gene encoding a carrier protein and wherein the carrier protein encoded by the second DNA sequence is one of:

(a) an *E. coli* protein having a predicted solubility probability of at least 90% based on a calculated value of $CV-CV_{bar} \leq -2.10$ wherein:

$$cv = \lambda_1\left(\frac{N+G+P+S}{n}\right) + \lambda_2\left|\frac{(R+K)-(D+E)}{n} - 0.03\right| \quad (I)$$

and
wherein:
- $CV_{bar}$ is the discriminant=1.71;
- n=total number of amino acids in the carrier protein;
- N, G, P, S=the number of Asn, Gly, Pro and Ser residues, respectively;
- R, K, D, E=the number of Arg, Lys, Asp, and Glu residues, respectively;
- $\gamma_1$=15.43 and $\gamma_2$ =−29.56; and (b) a protein which differs from the protein of (a) only by having one or more conservative amino acid substitutions wherein the predicted solubility probability of the carrier protein is not decreased below 90%.

2. A vector comprising the fusion DNA sequence of (a) of claim 1.

3. A host cell transformed or transfected with the vector of claim 2.

4. The host cell of claim 3 wherein the host cell is *E. coli*.

5. A vector comprising the fusion DNA sequence of (b) of claim 1.

6. A host cell transformed or transfected with the vector of claim 5.

7. The host cell of claim 6 wherein the host cell is *E. coli* or another bacterium.

8. The host cell of claim 6 wherein the host cell is a yeast, an insect cell, a mammalian cell or other eukaryotic cell.

9. The fusion DNA sequence of claim 1 wherein the first DNA sequence and second DNA sequence are linked via a linker DNA sequence encoding a linker peptide.

10. The fusion DNA sequence of claim 9 wherein the linker peptide encoded by the linker DNA sequence is cleavable.

11. A vector comprising the fusion DNA sequence of claim 1 and an expression control sequence operatively linked to the fusion DNA sequence.

12. The fusion DNA sequence of claim 1 wherein the second DNA sequence is selected from the group consisting of DNA sequences encoding *E. coli* protein RPSD, FTSY, AMY2, NUSA, GRPE, BFR, YJGD, YRFI, MAZG, and SSEB.

13. The fusion DNA sequence of claim 1 wherein the second DNA sequence is selected from the group consisting of DNA sequences encoding *E. coli* protein YCHA, YAGJ, YFBN, NARJ, NARW, YECA, CHEZ, SLYD, YJAG, and YIEJ.

14. The fusion DNA sequence of claim 1 wherein the second DNA sequence is selected from the group consisting of DNA sequences encoding *E. coli* proteins YGFB, YJDC, YCDY, AADB, FLAV, FLAW, YCED, YFHE, ASR, and YGGD.

15. The fusion DNA sequence of claim 1 wherein the second DNA sequence is selected from the group consisting of DNA sequences encoding *E. coli* protein YHBS, FTN, MENG, YBEL, S3AD, SMG, HYCI, SECB, YBEY, and ELAA.

16. The fusion DNA sequence of claim 1 wherein the second DNA sequence is selected from the group consisting of DNA sequences encoding *E. coli* protein YFJX, MIOC, HYFJ, RL16, RS6, YHHG, GCSH, TRD5, MSYB, RS12.

17. The fusion DNA sequence of claim 1 wherein the second DNA sequence is selected from the group consisting of DNA sequences encoding *E. coli* protein RL7, YACL, YBFG, RL20, HYPA, PTCA, YZPK, HYBF, and FER.

18. The fusion DNA sequence of claim 1 wherein the second DNA sequence is selected from the group consisting of DNA sequences encoding *E. coli* protein YR7J, YGGL, CYAY, YEHK, YR7G, YQFB, GLPE, YCCD, and RS14.

19. The fusion DNA sequence of claim 1 wherein the second DNA sequence encodes a protein wherein n is at least 100.

20. The fusion DNA sequence of claim 1 further comprising at least one additional copy of the second DNA sequence.

21. The fusion DNA sequence of claim 1 further comprising one or more copies of a third DNA sequence encoding an additional carrier protein, wherein the third DNA sequence is different from the second DNA sequence.

22. A method of producing a soluble heterologous protein, comprising:

culturing a host cell comprising the fusion DNA sequence of claim 1 under conditions causing expression of the fusion DNA sequence therein so that a fusion protein is produced;

recovering the expressed fusion protein from the cultured cell in a soluble fraction thereof; and cleaving the heterologous protein from the fusion protein and obtaining the heterologous protein in a substantially purified and soluble form.

23. The method of claim 22 wherein the host cell further comprises an expression control sequence operative linked to the fusion DNA sequence.

24. A fusion protein produced by the process of:

culturing a host cell comprising the fusion DNA sequence of claim 1 under conditions causing the expression of the fusion DNA sequence therein; and obtaining a fusion protein formed from expression of the fusion DNA sequence in a soluble fraction of the cultured host cell.

* * * * *

UNITED STATES PATENT AND TRADEMARK OFFICE
CERTIFICATE OF CORRECTION

PATENT NO. : 6,207,420 B1  
DATED : March 27, 2001  
INVENTOR(S) : Roger G. Harrison et al.

Page 1 of 4

It is certified that error appears in the above-identified patent and that said Letters Patent is hereby corrected as shown below:

<u>Column 4,</u>
Line 4, delete "$\gamma_1=15.43$" and substitute -- $\lambda_1=15.43$ --.
Line 5, delete "$\gamma_2=29.56$" and substitute -- $\lambda_2=29.56$ --.
TABLE 1, between lines 46 and 47, add a space between "HIFN-$\gamma$" and "Fusion Protein".

TABLE 1

Predicted Solubilities of Carrier, Target Proteins, and Carrier/Target Fusion Proteins. The carrier proteins have relatively high solubility probabilities while the target proteins (hIL-3, bGH, and hIFN-$\gamma$) do not.

| | MW (kDA) | Amino Acid Length | Probabilty of Solubility or Insolubility* |
|---|---|---|---|
| Protein | | | |
| 2X-YjgD | 31.2 | 276 | >97% soluble |
| NusA | 55.0 | 495 | 95% soluble |
| BFR | 18.5 | 158 | 95% soluble |
| GrpE | 21.7 | 197 | 92% soluble |
| thioredoxin | 11.7 | 109 | 73% soluble |
| hIL-3 | 15.1 | 133 | 73% insoluble |
| bGH | 21.6 | 189 | 85% insoluble |
| hIFN-$\gamma$ | 17.1 | 146 | 96% insoluble |
| Fusion Protein | | | |
| 2X-YjgD/hIL-3 | 47.3 | 417 | >97% soluble |
| NusA/hIL-3 | 70.6 | 634 | 86% soluble |
| NusA/bGH | 77.4 | 690 | 80% soluble |
| NusA/hIFN-$\gamma$ | 72.7 | 647 | 79% soluble |
| GrpE/hIL-3 | 37.3 | 336 | 72% soluble |
| BFR/hIL-3 | 34.1 | 297 | 72% soluble |
| thio/hIL-3 | 26.8 | 248 | 54% insoluble |

Note: the Ile-Glu-Gly-Arg sequence for factor Xa cleavage and the amino acids Thr-Gly created by an AgeI restriction site are included in the MW and solubility calculations.
*See Equations I and II

UNITED STATES PATENT AND TRADEMARK OFFICE
CERTIFICATE OF CORRECTION

PATENT NO.    : 6,207,420 B1
DATED         : March 27, 2001
INVENTOR(S)   : Roger G. Harrison et al.

It is certified that error appears in the above-identified patent and that said Letters Patent is hereby corrected as shown below:

Column 5,
TABLE 2, delete the space between "SWISS-PROT" and "Protein Name".

TABLE 2

*Escherichia coli* proteins of 100 amino acids or greater in length in the SWISS-PROT protein databank which have a calculated CV-CVbar value of −2.10 or less, which are predicted by the two parameter solubility model of Wilkinson and Harrison to have a solubility probability of 90% or greater when expressed in the *E. coli* cytoplasm.

| SWISS-PROT Protein Name | Total No. of Amino Acids | $CV\text{-}CV_{bar}$ | Arg | Asn | Asp | Glu | Gly | Lys | Pro | Ser |
|---|---|---|---|---|---|---|---|---|---|---|
| RPSD_ECOLI | 613 | −2.48 | 46 | 19 | 54 | 71 | 24 | 34 | 19 | 29 |
| FTSY_ECOLI | 497 | −3.15 | 18 | 11 | 22 | 79 | 30 | 33 | 22 | 15 |
| AMY2_ECOLI | 495 | −2.17 | 20 | 21 | 44 | 40 | 40 | 20 | 23 | 14 |
| NUSA_ECOLI | 495 | −2.62 | 33 | 19 | 42 | 56 | 28 | 25 | 14 | 15 |
| YRFI_ECOLI | 294 | −2.67 | 12 | 16 | 23 | 26 | 19 | 7 | 14 | 7 |
| MAZG_ECOLI | 263 | −3.03 | 21 | 7 | 21 | 32 | 10 | 12 | 7 | 7 |
| S3AD_ECOLI | 263 | −2.38 | 16 | 5 | 18 | 27 | 13 | 8 | 14 | 12 |
| SSEB_ECOLI | 261 | −2.24 | 9 | 6 | 12 | 34 | 17 | 13 | 15 | 14 |
| YCHA_ECOLI | 252 | −2.42 | 13 | 11 | 18 | 26 | 9 | 8 | 12 | 15 |
| YAGJ_ECOLI | 243 | −2.26 | 14 | 5 | 19 | 26 | 12 | 15 | 9 | 10 |
| YFBN_ECOLI | 238 | −2.65 | 15 | 10 | 19 | 23 | 9 | 13 | 4 | 3 |
| NARJ_ECOLI | 236 | −2.44 | 13 | 4 | 19 | 19 | 11 | 8 | 9 | 11 |
| NARW_ECOLI | 231 | −2.36 | 13 | 6 | 21 | 20 | 11 | 9 | 10 | 13 |
| YECA_ECOLI | 221 | −2.54 | 8 | 6 | 13 | 28 | 12 | 11 | 14 | 11 |
| CHEZ_ECOLI | 214 | −2.49 | 14 | 5 | 22 | 15 | 7 | 6 | 9 | 13 |
| GRPE_ECOLI | 197 | −2.34 | 11 | 8 | 13 | 26 | 8 | 13 | 9 | 7 |
| SLYD_ECOLI | 196 | −2.98 | 4 | 6 | 19 | 17 | 29 | 6 | 5 | 5 |
| YJAG_ECOLI | 196 | −3.33 | 11 | 5 | 12 | 25 | 9 | 6 | 5 | 10 |
| YIEJ_ECOLI | 195 | −2.77 | 6 | 6 | 16 | 21 | 17 | 10 | 8 | 7 |
| YGFB_ECOLI | 194 | −3.22 | 4 | 8 | 18 | 16 | 17 | 4 | 9 | 8 |
| YJDC_ECOLI | 191 | −2.13 | 15 | 4 | 15 | 15 | 7 | 6 | 7 | 5 |
| YCDY_ECOLI | 184 | −3.12 | 9 | 3 | 12 | 21 | 8 | 3 | 11 | 12 |
| AADB_ECOLI | 177 | −2.65 | 13 | 2 | 13 | 20 | 14 | 4 | 9 | 5 |
| FLAV_ECOLI | 175 | −4.09 | 4 | 4 | 20 | 17 | 15 | 9 | 5 | 5 |
| FLAW_ECOLI | 173 | −3.32 | 2 | 5 | 16 | 16 | 16 | 8 | 6 | 7 |
| YCED_ECOLI | 173 | −2.57 | 7 | 4 | 12 | 19 | 5 | 8 | 12 | 10 |
| YFHE_ECOLI | 171 | −2.62 | 13 | 2 | 14 | 16 | 3 | 8 | 3 | 9 |
| ASR_ECOLI | 169 | −2.62 | 14 | 8 | 0 | 5 | 5 | 18 | 10 | 9 |
| YGGD_ECOLI | 169 | −2.76 | 4 | 6 | 17 | 9 | 5 | 8 | 5 | 9 |
| YHBS_ECOLI | 167 | −2.39 | 11 | 3 | 15 | 13 | 16 | 2 | 6 | 6 |
| FTN_ECOLI | 165 | −2.21 | 4 | 8 | 7 | 19 | 5 | 9 | 4 | 12 |
| MENG_ECOLI | 161 | −2.44 | 8 | 7 | 15 | 14 | 21 | 2 | 3 | 7 |
| YBEL_ECOLI | 160 | −2.13 | 14 | 4 | 9 | 22 | 7 | 7 | 5 | 8 |
| BFR_ECOLI | 158 | −2.68 | 9 | 10 | 14 | 18 | 11 | 9 | 1 | 4 |
| SMG_ECOLI | 157 | −5.53 | 7 | 6 | 12 | 23 | 5 | 3 | 4 | 3 |
| HYCI_ECOLI | 156 | −2.55 | 5 | 7 | 14 | 13 | 16 | 4 | 10 | 2 |
| SECB_ECOLI | 155 | −2.18 | 4 | 7 | 8 | 13 | 9 | 3 | 7 | 8 |
| YBEY_ECOLI | 155 | −4.29 | 3 | 4 | 9 | 23 | 8 | 5 | 8 | 9 |

UNITED STATES PATENT AND TRADEMARK OFFICE
CERTIFICATE OF CORRECTION

PATENT NO. : 6,207,420 B1
DATED : March 27, 2001
INVENTOR(S) : Roger G. Harrison et al.

It is certified that error appears in the above-identified patent and that said Letters Patent is hereby corrected as shown below:

Column 5,
TABLE 2, continued

| | | | | | | | | | | |
|---|---|---|---|---|---|---|---|---|---|---|
| ELAA_ECOLI | 153 | -2.39 | 6 | 4 | 12 | 12 | 10 | 5 | 6 | 7 |
| YFJX_ECOLI | 152 | -2.37 | 6 | 5 | 11 | 11 | 11 | 1 | 7 | 8 |
| MIOC_ECOLI | 146 | -2.23 | 2 | 4 | 10 | 16 | 15 | 7 | 7 | 10 |
| YJGD_ECOLI | 138 | -9.37 | 3 | 3 | 22 | 25 | 8 | 3 | 4 | 3 |
| HYFJ_ECOLI | 137 | -2.51 | 7 | 1 | 7 | 13 | 5 | 4 | 4 | 8 |
| RL16_ECOLI | 136 | -2.45 | 14 | 2 | 3 | 7 | 13 | 16 | 7 | 2 |
| RS6_ECOLI | 135 | -3.17 | 12 | 4 | 10 | 20 | 5 | 6 | 5 | 4 |
| YHHG_ECOLI | 133 | -2.17 | 10 | 3 | 14 | 7 | 7 | 3 | 1 | 8 |
| GCSH_ECOLI | 129 | -4.06 | 1 | 3 | 11 | 17 | 8 | 6 | 5 | 12 |
| TRD5_ECOLI | 129 | -4.88 | 6 | 3 | 16 | 15 | 8 | 2 | 10 | 4 |
| MSYB_ECOLI | 124 | -8.22 | 4 | 4 | 14 | 24 | 8 | 1 | 4 | 2 |
| RS12_ECOLI | 123 | -2.23 | 15 | 5 | 3 | 4 | 11 | 13 | 7 | 6 |
| RL7_ECOLI | 120 | -2.38 | 1 | 1 | 6 | 16 | 8 | 13 | 2 | 6 |
| YACL_ECOLI | 120 | -3.85 | 6 | 5 | 7 | 18 | 9 | 4 | 0 | 5 |
| YBFO_ECOLI | 120 | -3.11 | 5 | 3 | 8 | 12 | 7 | 3 | 3 | 6 |
| RL20_ECOLI | 117 | -5.17 | 16 | 3 | 4 | 2 | 6 | 14 | 0 | 4 |
| HYPA_ECOLI | 116 | -2.27 | 8 | 0 | 5 | 12 | 7 | 4 | 1 | 4 |
| PTCA_ECOLI | 116 | -2.64 | 3 | 3 | 7 | 12 | 6 | 8 | 1 | 5 |
| YZFK_ECOLI | 115 | -2.76 | 23 | 2 | 2 | 5 | 8 | 3 | 5 | 7 |
| HYBF_ECOLI | 113 | -2.90 | 5 | 0 | 6 | 11 | 5 | 3 | 2 | 8 |
| FER_ECOLI | 110 | -3.41 | 6 | 3 | 9 | 14 | 5 | 3 | 6 | 7 |
| YR7J_ECOLI | 110 | -2.33 | 8 | 2 | 1 | 1 | 4 | 9 | 5 | 7 |
| GLPE_ECOLI | 108 | -2.35 | 3 | 4 | 10 | 5 | 8 | 3 | 3 | 4 |
| YGGL_ECOLI | 108 | -2.23 | 8 | 3 | 8 | 15 | 6 | 8 | 2 | 5 |
| CYAY_ECOLI | 106 | -3.74 | 5 | 4 | 12 | 10 | 9 | 3 | 1 | 5 |
| YEHK_ECOLI | 105 | -2.50 | 11 | 4 | 8 | 14 | 2 | 3 | 6 | 4 |
| YR7G_ECOLI | 105 | -4.14 | 3 | 3 | 13 | 12 | 7 | 4 | 7 | 7 |
| YQFB_ECOLI | 103 | -2.81 | 5 | 2 | 9 | 9 | 5 | 6 | 2 | 3 |
| YCCD_ECOLI | 101 | -2.52 | 8 | 3 | 5 | 10 | 4 | 1 | 3 | 2 |
| RS14_ECOLI | 100 | -2.17 | 14 | 3 | 5 | 5 | 5 | 11 | 4 | 8 |

Page 3 of 4

UNITED STATES PATENT AND TRADEMARK OFFICE
CERTIFICATE OF CORRECTION

PATENT NO. : 6,207,420 B1
DATED : March 27, 2001
INVENTOR(S) : Roger G. Harrison et al.

It is certified that error appears in the above-identified patent and that said Letters Patent is hereby corrected as shown below:

Column 14,
Line 62, delete "gene" and substitute -- DNA sequence --.

Column 15,
Line 13, delete "$\gamma_1=15.43$ and $\gamma_2=29.56$" and substitute -- $\lambda_1=15.43$ and $\lambda_2=29.56$ --.

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,207,420 B1
APPLICATION NO. : 09/448224
DATED : March 27, 2001
INVENTOR(S) : Roger G. Harrison et al.

It is certified that error appears in the above-identified patent and that said Letters Patent is hereby corrected as shown below:

Column 4,
Line 4, delete "$\gamma_1=15.43$" and substitute -- $\lambda_1=15.43$ --.
Line 5, delete "$\gamma_2=29.56$" and substitute -- $\lambda_2=-29.56$ --.
TABLE 1, between lines 46 and 47, add a space between "HIFN-$\gamma$" and "Fusion Protein".

TABLE 1

Predicted Solubilities of Carrier, Target Proteins, and Carrier/Target Fusion Proteins. The carrier proteins have relatively high solubility probabilites while the target proteins (hIL-3, bGH, and hIFN-$\gamma$) do not.

| | MW (kDA) | Amino Acid Length | Probability of Solubility or Insolubility* |
|---|---|---|---|
| Protein | | | |
| 2X-YjgD | 31.2 | 276 | >97% soluble |
| NusA | 55.0 | 495 | 95% soluble |
| BFR | 18.5 | 158 | 95% soluble |
| GrpE | 21.7 | 197 | 92% soluble |
| thioredoxin | 11.7 | 109 | 73% soluble |
| hIL-3 | 15.1 | 133 | 73% insoluble |
| bGH | 21.6 | 189 | 85% insoluble |
| hIFN-$\gamma$ | 17.1 | 146 | 96% insoluble |
| Fusion Protein | | | |
| 2X-YjgD/hIL-3 | 47.3 | 417 | >97% soluble |
| NusA/hIL-3 | 70.6 | 634 | 86% soluble |
| NusA/bGH | 77.4 | 690 | 80% soluble |
| NusA/hIFN$\gamma$ | 72.7 | 647 | 79% soluble |
| GrpE/hIL-3 | 37.3 | 336 | 72% soluble |
| BFR/hIL-3 | 34.1 | 297 | 72% soluble |
| thio/hIL-3 | 26.8 | 248 | 54% insoluble |

Note: the Ile-Glu-Gly-Arg sequence for factor Xa cleavage and the amino acids Thr-Gly created by an AgeI restriction site are included in the MW and solubility calculations.
*See Equations I and II

UNITED STATES PATENT AND TRADEMARK OFFICE
CERTIFICATE OF CORRECTION

PATENT NO. : 6,207,420 B1
APPLICATION NO. : 09/448224
DATED : March 27, 2001
INVENTOR(S) : Roger G. Harrison et al.

It is certified that error appears in the above-identified patent and that said Letters Patent is hereby corrected as shown below:

Column 5,
TABLE 2, delete the space between "SWISS-PROT" and "Protein Name".

TABLE 2

*Escherichia coli* proteins of 100 amino acids or greater in length in the SWISS-PROT protein databank which have a calculated CV-CVbar value of -2.10 or less, which are predicted by the two parameter solubility model of Wilkinson and Harrison to have a solubility probability of 90% or greater when expressed in the *E. coli* cytoplasm.

| SWISS-PROT Protein Name | Total No. of Amino Acids | CV-CV$_{bar}$ | \multicolumn{8}{c}{Amino Acids used for CV-CV$_{bar}$ calculation} |
|---|---|---|---|---|---|---|---|---|---|---|
| | | | Arg | Asn | Asp | Glu | Gly | Lys | Pro | Ser |
| RPSD_ECOLI | 613 | -2.48 | 46 | 19 | 54 | 71 | 24 | 34 | 19 | 29 |
| FTSY_ECOLI | 497 | -3.15 | 18 | 11 | 22 | 79 | 30 | 33 | 22 | 15 |
| AMY2_ECOLI | 495 | -2.17 | 20 | 21 | 44 | 40 | 40 | 20 | 23 | 14 |
| NUSA_ECOLI | 495 | -2.62 | 33 | 19 | 42 | 56 | 28 | 25 | 14 | 15 |
| YRFL_ECOLI | 294 | -2.67 | 12 | 16 | 23 | 26 | 19 | 7 | 14 | 7 |
| MAZG_ECOLI | 263 | -3.03 | 21 | 7 | 21 | 32 | 10 | 12 | 7 | 7 |
| S3AD_ECOLI | 263 | -2.38 | 16 | 5 | 18 | 27 | 13 | 8 | 14 | 12 |
| SSEB_ECOLI | 261 | -2.24 | 9 | 6 | 12 | 34 | 17 | 13 | 15 | 14 |
| YCHA_ECOLI | 252 | -2.42 | 13 | 11 | 18 | 26 | 9 | 8 | 12 | 15 |
| YAGJ_ECOLI | 243 | -2.26 | 14 | 5 | 19 | 26 | 12 | 15 | 9 | 10 |
| YFBN_ECOLI | 238 | -2.65 | 15 | 10 | 19 | 23 | 9 | 13 | 4 | 3 |
| NARJ_ECOLI | 236 | -2.44 | 13 | 4 | 19 | 19 | 11 | 8 | 9 | 11 |
| NARW_ECOLI | 231 | -2.36 | 13 | 6 | 21 | 20 | 11 | 9 | 10 | 13 |
| YECA_ECOLI | 221 | -2.54 | 8 | 6 | 13 | 28 | 12 | 11 | 14 | 11 |
| CHEZ_ECOLI | 214 | -2.49 | 14 | 5 | 22 | 15 | 7 | 6 | 9 | 13 |
| GRPE_ECOLI | 197 | -2.34 | 11 | 8 | 13 | 26 | 8 | 13 | 9 | 7 |
| SLYD_ECOLI | 196 | -2.98 | 4 | 6 | 19 | 17 | 29 | 6 | 5 | 5 |
| YJAG_ECOLI | 196 | -3.33 | 11 | 5 | 12 | 25 | 9 | 6 | 5 | 10 |
| YIEJ_ECOLI | 195 | -2.77 | 6 | 6 | 16 | 21 | 17 | 10 | 8 | 7 |
| YGFB_ECOLI | 194 | -3.22 | 4 | 8 | 18 | 16 | 17 | 4 | 9 | 8 |
| YJDC_ECOLI | 191 | -2.13 | 15 | 4 | 15 | 15 | 7 | 6 | 7 | 5 |
| YCDY_ECOLI | 184 | -3.12 | 9 | 3 | 12 | 21 | 8 | 3 | 11 | 12 |
| AADB_ECOLI | 177 | -2.65 | 13 | 2 | 13 | 20 | 14 | 4 | 9 | 5 |
| FLAV_ECOLI | 175 | -4.09 | 4 | 4 | 20 | 17 | 15 | 9 | 5 | 5 |
| FLAW_ECOLI | 173 | -3.32 | 2 | 5 | 16 | 16 | 16 | 8 | 6 | 7 |
| YCED_ECOLI | 173 | -2.57 | 7 | 4 | 12 | 19 | 5 | 8 | 12 | 10 |
| YFHE_ECOLI | 171 | -2.62 | 13 | 2 | 14 | 16 | 3 | 8 | 3 | 9 |
| ASR_ECOLI | 169 | -2.62 | 14 | 8 | 0 | 5 | 5 | 18 | 10 | 9 |
| YGGD_ECOLI | 169 | -2.76 | 4 | 6 | 17 | 9 | 5 | 8 | 5 | 9 |
| YHBS_ECOLI | 167 | -2.39 | 11 | 3 | 15 | 13 | 16 | 2 | 6 | 6 |
| FTN_ECOLI | 165 | -2.21 | 4 | 8 | 7 | 19 | 5 | 9 | 4 | 12 |
| MENG_ECOLI | 161 | -2.44 | 8 | 7 | 15 | 14 | 21 | 2 | 3 | 7 |
| YBEL_ECOLI | 160 | -2.13 | 14 | 4 | 9 | 22 | 7 | 7 | 5 | 8 |
| BFR_ECOLI | 158 | -2.68 | 9 | 10 | 14 | 18 | 11 | 9 | 1 | 4 |
| SMG_ECOLI | 157 | -5.53 | 7 | 6 | 12 | 23 | 5 | 3 | 4 | 3 |
| HYC1_ECOLI | 156 | -2.55 | 5 | 7 | 14 | 13 | 16 | 4 | 10 | 2 |
| SECB_ECOLI | 155 | -2.18 | 4 | 7 | 8 | 13 | 9 | 3 | 7 | 8 |
| YBEY_ECOLI | 155 | -4.29 | 3 | 4 | 9 | 23 | 8 | 5 | 8 | 9 |

UNITED STATES PATENT AND TRADEMARK OFFICE
CERTIFICATE OF CORRECTION

PATENT NO. : 6,207,420 B1
APPLICATION NO. : 09/448224
DATED : March 27, 2001
INVENTOR(S) : Roger G. Harrison et al.

It is certified that error appears in the above-identified patent and that said Letters Patent is hereby corrected as shown below:

Column 5,
TABLE 2, continued

| | | | | | | | | | | |
|---|---|---|---|---|---|---|---|---|---|---|
| ELAA_ECOLI | 153 | -2.39 | 6 | 4 | 12 | 12 | 10 | 5 | 6 | 7 |
| YFIX_ECOLI | 152 | -2.37 | 6 | 5 | 11 | 11 | 11 | 1 | 7 | 8 |
| MIOC_ECOLI | 146 | -2.23 | 2 | 4 | 10 | 16 | 15 | 7 | 7 | 10 |
| YIGD_ECOLI | 138 | -9.37 | 3 | 3 | 22 | 25 | 8 | 3 | 4 | 3 |
| HYFJ_ECOLI | 137 | -2.51 | 7 | 1 | 7 | 13 | 5 | 4 | 4 | 8 |
| RL16_ECOLI | 136 | -2.45 | 14 | 2 | 3 | 7 | 13 | 16 | 7 | 2 |
| RS6_ECOLI | 135 | -3.17 | 12 | 4 | 10 | 20 | 5 | 6 | 5 | 4 |
| YHHG_ECOLI | 133 | -2.17 | 10 | 3 | 14 | 7 | 7 | 3 | 1 | 8 |
| GCSH_ECOLI | 129 | -4.06 | 1 | 3 | 11 | 17 | 8 | 6 | 5 | 12 |
| TRD5_ECOLI | 129 | -4.88 | 6 | 3 | 16 | 15 | 8 | 2 | 10 | 4 |
| MSYB_ECOLI | 124 | -8.22 | 4 | 4 | 14 | 24 | 8 | 1 | 4 | 2 |
| RS12_ECOLI | 123 | -2.23 | 15 | 5 | 3 | 4 | 11 | 13 | 7 | 6 |
| RL7_ECOLI | 120 | -2.38 | 1 | 1 | 6 | 16 | 8 | 13 | 2 | 6 |
| YACL_ECOLI | 120 | -3.85 | 6 | 5 | 7 | 18 | 9 | 4 | 0 | 5 |
| YBFG_ECOLI | 120 | -3.31 | 5 | 3 | 8 | 12 | 7 | 3 | 3 | 6 |
| RL20_ECOLI | 117 | -5.17 | 16 | 3 | 4 | 2 | 6 | 14 | 0 | 4 |
| HYPA_ECOLI | 116 | -2.27 | 8 | 0 | 5 | 12 | 7 | 4 | 1 | 4 |
| PTCA_ECOLI | 116 | -2.64 | 3 | 3 | 7 | 12 | 6 | 8 | 1 | 5 |
| YZFK_ECOLI | 115 | -2.76 | 23 | 2 | 2 | 5 | 8 | 3 | 5 | 7 |
| HYBF_ECOLI | 113 | -2.90 | 5 | 0 | 6 | 11 | 5 | 3 | 2 | 8 |
| FER_ECOLI | 110 | -3.41 | 6 | 3 | 9 | 14 | 5 | 3 | 6 | 7 |
| YR7J_ECOLI | 110 | -2.33 | 8 | 2 | 1 | 1 | 4 | 9 | 5 | 7 |
| GLPE_ECOLI | 108 | -2.35 | 3 | 4 | 10 | 5 | 8 | 3 | 3 | 4 |
| YGGL_ECOLI | 108 | -2.23 | 8 | 3 | 8 | 15 | 6 | 8 | 2 | 5 |
| CYAY_ECOLI | 106 | -3.74 | 5 | 4 | 12 | 10 | 9 | 3 | 1 | 5 |
| YEHK_ECOLI | 105 | -2.50 | 11 | 4 | 8 | 14 | 2 | 3 | 6 | 4 |
| YR7G_ECOLI | 105 | -4.14 | 3 | 3 | 13 | 12 | 7 | 4 | 7 | 7 |
| YQFB_ECOLI | 103 | -2.81 | 5 | 2 | 9 | 9 | 5 | 6 | 2 | 3 |
| YCCD_ECOLI | 101 | -2.52 | 8 | 3 | 5 | 10 | 4 | 1 | 3 | 2 |
| RS14_ECOLI | 100 | -2.17 | 14 | 3 | 5 | 5 | 5 | 11 | 4 | 8 |

UNITED STATES PATENT AND TRADEMARK OFFICE
CERTIFICATE OF CORRECTION

PATENT NO. : 6,207,420 B1
APPLICATION NO. : 09/448224
DATED : March 27, 2001
INVENTOR(S) : Roger G. Harrison et al.

It is certified that error appears in the above-identified patent and that said Letters Patent is hereby corrected as shown below:

Column 14,
Line 62, delete "gene" and substitute -- DNA sequence --.

Column 15,
Line 13, delete "$\gamma_1=15.43$ and $\gamma_2=29.56$" and substitute -- $\lambda_1=15.43$ and $\lambda_2=-29.56$ --.

This certificate supersedes the Certificate of Correction issued December 28, 2004.

Signed and Sealed this

Sixteenth Day of June, 2009

JOHN DOLL
*Acting Director of the United States Patent and Trademark Office*